United States Patent
Bourne (10) Patent No.: US 11,944,846 B2
(45) Date of Patent: Apr. 2, 2024

(54) MAGNETIC RESONANCE IMAGING SYSTEM WITH MOVABLY SUSPENDED RECEIVE COIL

(71) Applicant: Elekta Limited, Crawley (GB)

(72) Inventor: Duncan Bourne, Sussex (GB)

(73) Assignee: Elekta Limited, Crawley (GB)

( * ) Notice: Subject to any disclaimer, the term of this patent is extended or adjusted under 35 U.S.C. 154(b) by 689 days.

(21) Appl. No.: 17/250,016

(22) PCT Filed: May 3, 2019

(86) PCT No.: PCT/EP2019/061434
§ 371 (c)(1),
(2) Date: Nov. 3, 2020

(87) PCT Pub. No.: WO2019/215050
PCT Pub. Date: Nov. 14, 2019

(65) Prior Publication Data
US 2021/0236852 A1    Aug. 5, 2021

(30) Foreign Application Priority Data
May 8, 2018   (GB) ..................................... 1807507

(51) Int. Cl.
*A61N 5/10*      (2006.01)
*G01R 33/34*   (2006.01)
*G01R 33/48*   (2006.01)

(52) U.S. Cl.
CPC ..... *A61N 5/1049* (2013.01); *G01R 33/34007* (2013.01); *G01R 33/4808* (2013.01); *A61N 2005/1055* (2013.01)

(58) Field of Classification Search
CPC .......... A61N 5/1049; A61N 2005/1055; G01R 33/34007; G01R 33/4808
See application file for complete search history.

(56) References Cited

U.S. PATENT DOCUMENTS

| | | | |
|---|---|---|---|
| 6,323,749 B1 * | 11/2001 | Hsieh | H01F 6/00 335/216 |
| 2002/0138001 A1 * | 9/2002 | Kroeckel | G01R 33/34084 600/410 |

(Continued)

FOREIGN PATENT DOCUMENTS

| CN | 201398969 Y | 2/2010 |
|---|---|---|
| GB | 2531591 A | 4/2016 |
| JP | 2008005999 A | 1/2008 |

OTHER PUBLICATIONS

"International Application Serial No. PCT/EP2019/061434, International Search Report dated Aug. 8, 2019", (Aug. 8, 2019), 5 pgs.

(Continued)

*Primary Examiner* — Dixomara Vargas
(74) *Attorney, Agent, or Firm* — Schwegman Lundberg & Woessner, P.A.

(57) ABSTRACT

Embodiments of the disclosure provide a medical apparatus (100), comprising: a structure defining a bore (104) in which a patient or part of a patient can be positioned during use; an MRI system comprising: a receiving coil device (116) positioned within the bore, the receiving coil device (116) comprising a receiving coil for detecting radio signals emitted by relaxing nuclei within the patient; a constraining mechanism (118) coupled between the structure and the receiving coil device (116), the constraining mechanism (118) permitting movement of the receiving coil device (116) in a single linear dimension; and one or more retractable suspension mounts (120a, 120b), each of the one or more retractable suspension mounts (120a, 120b) comprising a flexible line arranged to suspend at least part of the receiving coil device (116) within the bore.

20 Claims, 4 Drawing Sheets

(56) References Cited

U.S. PATENT DOCUMENTS

| | | | |
|---|---|---|---|
| 2005/0122108 A1* | 6/2005 | Yasuhara | G01R 33/341 |
| | | | 324/318 |
| 2005/0242814 A1* | 11/2005 | Schaaf | G01R 33/385 |
| | | | 324/318 |
| 2006/0106302 A1* | 5/2006 | Takamori | G01R 33/28 |
| | | | 600/415 |
| 2015/0293188 A1* | 10/2015 | Haider | G01R 33/34007 |
| | | | 324/322 |
| 2016/0113570 A1 | 4/2016 | Trausch et al. | |
| 2018/0035911 A1 | 2/2018 | Nousiainen | |

OTHER PUBLICATIONS

"International Application Serial No. PCT/EP2019/061434, Written Opinion dated Aug. 8, 2019", (Aug. 8, 2019), 11 pgs.
"United Kingdom Application Serial No. 1807507.7, Office Action dated Oct. 31, 2018", (Oct. 31, 2018), 8 pgs.

* cited by examiner

MAGNETIC RESONANCE IMAGING SYSTEM WITH MOVABLY SUSPENDED RECEIVE COIL

PRIORITY APPLICATIONS

This application is a U.S. National Stage Filing under 35 U.S.C. § 371 from International Application No. PCT/EP2019/061434, filed on May 3, 2019, and published as WO2019/215050 on Nov. 14, 2019, which claims the benefit of priority to United Kingdom Application No. 1807507.7, filed on May 8, 2018; the benefit of priority of each of which is hereby claimed herein, and which applications and publication are hereby incorporated herein by reference in their entirety.

TECHNICAL FIELD

Embodiments of the present disclosure relate to medical methods and apparatus, and particularly to a medical apparatus comprising an MRI system, and corresponding methods.

BACKGROUND

Recent developments in the field of radiotherapy have focused on integrating an imaging system with the therapeutic system. The goal is to provide real-time, or near real-time, feedback on the location of an anatomical feature within the patient (e.g. a tumour) such that a therapeutic radiation beam can be more accurately controlled to target that feature, or therapy can be halted if the radiation beam has become misdirected (for example).

One suggested approach is to combine a linear accelerator-based therapeutic system with a magnetic resonance imaging (MRI) system within a single apparatus, known as an MRI-Linac. Such apparatus is described in a number of earlier applications by the present Applicant, including U.S. patent application Ser. No. 12/704,944 (publication no 2011/0201918) and PCT publication no 2011/127947. In the systems described in these earlier applications, a patient can be imaged and treated substantially simultaneously while lying in the same position.

One feature of the MRI system is a transmitter/receiver coil (also known as an "imaging coil"). A transmitter/receiver coil device typically comprises a transmitter/receiver coil (i.e. a coil of wire) and associated processing circuitry, and acts to detect the low-amplitude radio-frequency electromagnetic signals generated within the patient as part of the MRI process. In a conventional MRI system, the transmitter/receiver coil is placed directly on the patient so as to maximise the efficiency with which those signals are detected. For example, it is known to manufacture transmitter/receiver coils using a certain geometry so as to fit closely to certain parts of the human anatomy. One such class of coil is known as an anterior coil, designed to fit closely to the front of a patient (e.g. the patient's chest, or torso region).

In a combined radiotherapy and MRI system, however, this solution is not advisable [A1] as the interaction of the radiation beam with the transmitter/receiver coil generates secondary electrons which would increase the dose in the skin of the patient. Further, while precise placement of the transmitter/receiver coil in an MRI system is generally not essential to performance of the system, damage to the processing circuitry of the device may result from its inaccurate placement in a combined radiotherapy and MRI system (i.e., through adverse interaction between the processing circuitry and the radiation beam).

SUMMARY

Embodiments of the present disclosure seek to alleviate or overcome some or all of these problems.

In one aspect, the present disclosure provides a medical apparatus, comprising: a structure defining a bore in which a patient or part of a patient can be positioned during use; an MRI system comprising: a receiving coil device positioned within the bore, the receiving coil device comprising a receiving coil for detecting radio signals emitted by relaxing nuclei within the patient; a constraining mechanism coupled between the structure and the receiving coil device, the constraining mechanism permitting movement of the receiving coil device in a single linear dimension; and one or more retractable suspension mounts, each of the one or more retractable suspension mounts comprising a flexible line arranged to suspend at least part of the receiving coil device within the bore.

BRIEF DESCRIPTION OF THE DRAWINGS

For a better understanding of the present disclosure, and to show more clearly how it may be carried into effect, reference will now he made, by way of example, to the following drawings, in which.

DETAILED DESCRIPTION

Figure 1:
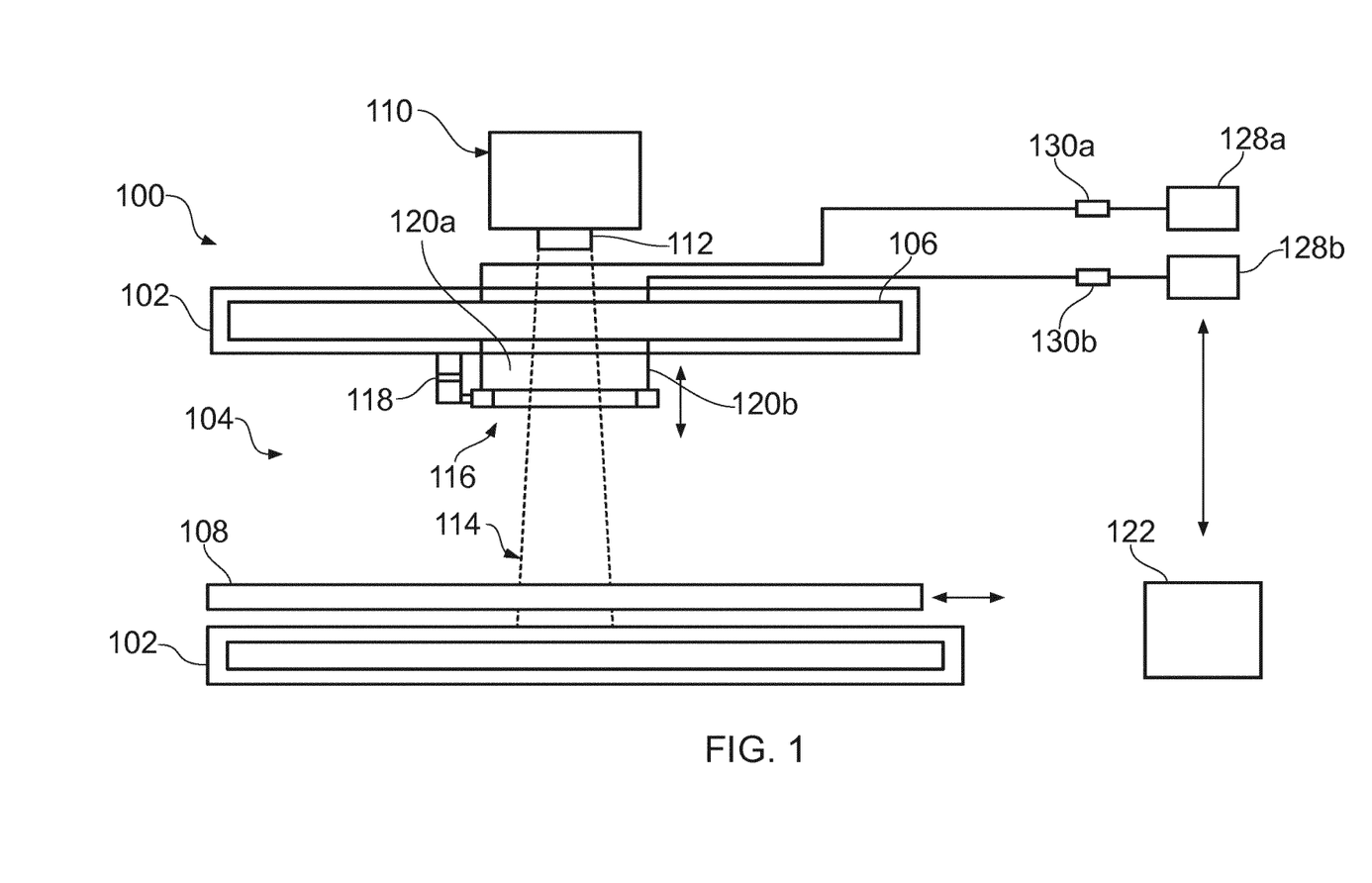
FIG. 1 shows a side view of a combined radiotherapy and MRI system in cross-section according to embodiments of the present disclosure.
Figure 2:
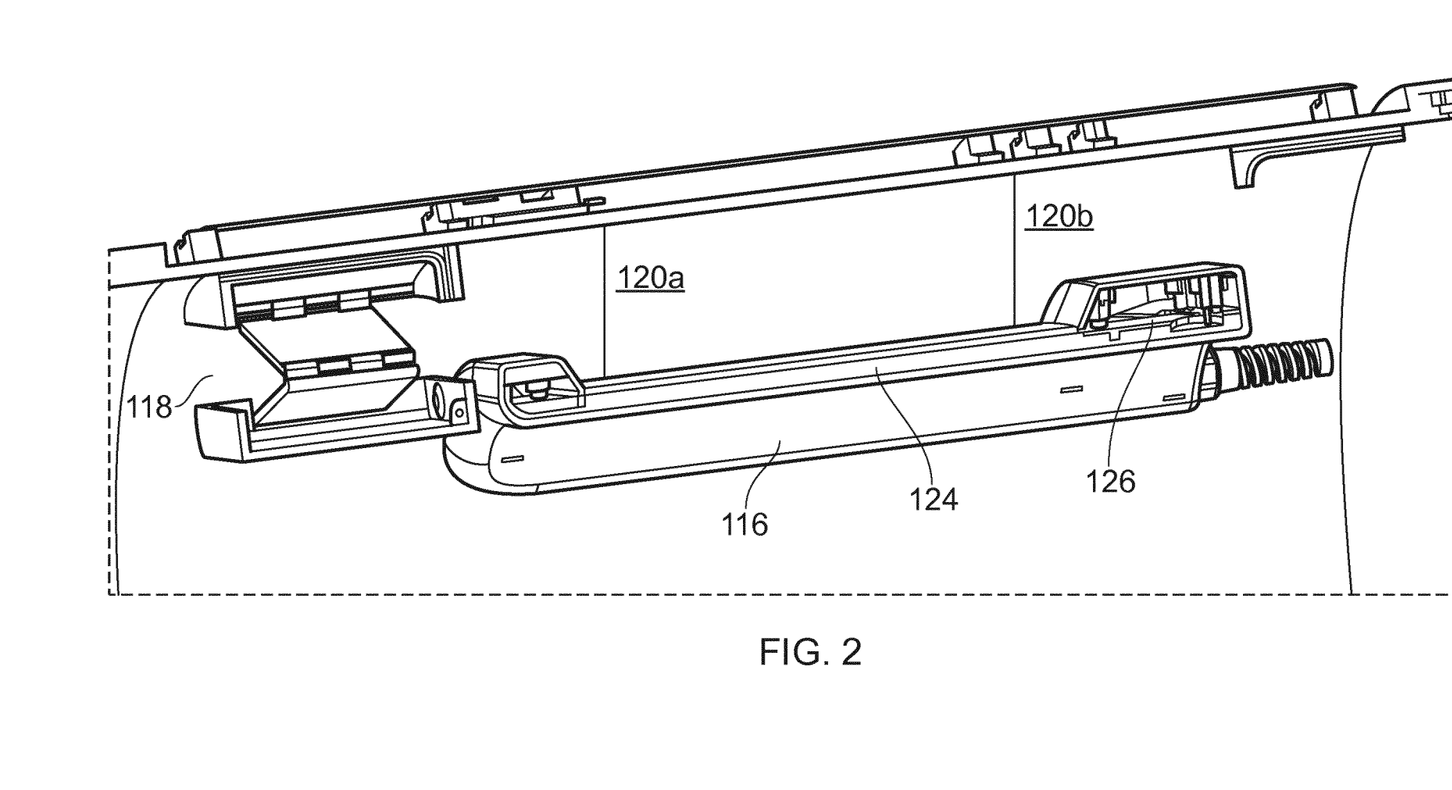
FIG. 2 shows a perspective view of a combined radiotherapy and MRI system in cross-section according to embodiments of the present disclosure.

FIG. 1 is a schematic illustration of a combined radiotherapy and MRI system 100 according to embodiments of the present disclosure, showing a side view of the system in cross-section. FIG. 2 shows a perspective view of part of the system 100, particularly the transmitter/receiver coil. Those skilled in the art will appreciate that certain features of the system have been omitted from one or other of the Figures for clarity purposes.

The system comprises a structure 102 defining a bore 104 in which a patient or part of a patient may be positioned during treatment. The bore 104 comprises a volume having any shape. For example, the bore 104 may be cylindrical or cuboid. The structure may comprise one or more coils 106 for generating a magnetic field as will be described in greater detail below.

A bed 108, for supporting the patient, can be positioned within the bore 104, and may be movable in a longitudinal direction into and out of the bore 104 to enable the patient to enter and exit the system 100 before and after treatment. A low-friction surface (for example, one or more rolling elements such as rollers) and a driving mechanism (such as a driving piston, or a pulley) may be provided to enable such movement.

The system 100 further comprises a radiotherapy apparatus which delivers doses of radiation to a patient supported by the bed 108. The radiotherapy apparatus comprises a radiation head 110 housing a source of radiation and a collimating device 112, which together generate a beam of therapeutic radiation 114. The source of radiation may take any suitable form (e.g. a radioactive source such as cobalt 60, a linear accelerator possibly in conjunction with an x-ray source, etc), and the beam may be formed of any suitable ionizing radiation, such as x-rays, electrons or protons (for example). The radiation will typically have an energy which is capable of having a therapeutic effect in a patient positioned on the bed 108. For example, a therapeutic x-ray beam may have an energy in excess of 1 MeV.

The collimating device 112 may be any device suitable for collimating the radiation beam to take a desired shape (for example, to conform to the shape of a target within the patient). In one embodiment, the collimating device may comprise a primary collimator and a second collimator. The primary collimator collimates the radiation to form a uniform beam shape (for example, cone-, fan- and pyramid-shaped beams are known in the art) and is typically fixed during treatment, while the secondary collimator acts on the beam so collimated to adjust the shape to conform to the cross-sectional shape or a target within the patient (e.g. a tumour) and may be adjustable during treatment. In one embodiment, the secondary collimating device comprises a multi-leaf collimator, known to those skilled in the art. Such a device comprises one or more banks of elongate leaves (and typically comprises two such banks on opposite sides of the beam), with each leaf being individually moveable into and out of the radiation beam in order to block that part of the beam from reaching the patient. In combination, the leaves collectively act to shape the beam according to a desired cross-section.

The radiation head may be mounted on a chassis (not illustrated), and configured such that the radiation beam 114 is directed towards the patient. The chassis may be rotatable around an axis, with the point of intersection of the radiation beam with the axis being known as the "isocentre" of the apparatus. In this way, radiation can be directed towards a patient on the bed 108 from multiple directions, reducing the dose which is delivered to healthy tissue surrounding the target for treatment.

The system 100 further comprises an MRI apparatus, for producing images of a patient positioned on the bed 108. The MRI apparatus includes one or more magnetic coils 106 which act to generate a magnetic field for magnetic resonance imaging. That is, the magnetic field lines generated by operation of the magnetic coil 106 run substantially parallel to the central axis of the bore. The magnetic coils 106 may consist of one or more coils with an axis that runs parallel to, or is coincident with the axis of rotation of the chassis. The magnetic coils may be split into first and second magnetic coils, each having a common central axis, but separated by a window which is free of coils. In other embodiments, the magnetic coils 106 may simply be thin enough that they are substantially transparent to radiation of the wavelength generated by the radiation head 110. In yet further embodiments, the magnetic coils 106 may have a varying pitch, such that the pitch is relatively wide where the coils 106 intersect with the radiation beam 114, and relatively narrow in one or more regions outside the radiation beam 114. The magnetic coils may comprise one or more coils for generating a primary magnetic field; one or more coils for generating a gradient magnetic field that is superposed on the primary magnetic field and allows spatial encoding of the protons so that their position can be determined from the frequency at which resonance occurs (the Larmor frequency); and/or one or more active shielding coils, which generate a magnetic field outside the apparatus of approximately equal magnitude and opposite polarity to the magnetic field generated by the primary magnetic coil. The more sensitive parts of the system 100, such as the radiation head 110, may be positioned in this region outside the coils where the magnetic field is cancelled, at least to a first order.

The coils 106 may be arranged within the structure 102, which can additionally contain a system for keeping the coils cool (e.g. a cryogenic system based on liquid helium or similar).

In use, the MRI system can provide real-time imaging of a patient undergoing therapy, allowing accurate targeting of the treatment volume by the radiation beam 114 (for example through altered collimation by the collimating device 112), or automated shutdown if the patient moves significantly.

One component of the MRI system which has not been discussed above is the RF system. This transmits radio signals towards the patient, and detects the absorption at those frequencies so that the presence and location of protons in the patient can be determined. The RF system may include a single coil that both transmits the radio signals and receives the reflected signals, dedicated transmitting and receiving coils, or multi-element phased array coils, for example. As described above, it is important that the imaging coil be arranged as close to the patient as possible, so as to detect the low-amplitude signals which are emitted by the protons within the patient.

FIGS. 1 and 2 show an imaging coil device 116 according to embodiments of the disclosure.

The imaging coil device is suspended by first and second retractable suspension mounts 120a, 120b, each comprising a flexible line. Non-conductive materials may be used so as not to interfere with the magnetic field generated by the MRI system.

In the illustrated embodiment, the first suspension mount 120a is coupled to the imaging coil device 116 at or towards a first end of the imaging coil device 116, while the second suspension mount 120b is coupled to the imaging coil device 116 at or towards a second, opposing end of the imaging coil device 116.

As noted above, each of the suspension mounts 120a, 120b comprises a flexible mechanical line, held under tension by the weight of the imaging coil device 116. For example, the flexible line may comprise a wire or cable (or string or rope), manufactured from non-conductive material to avoid interactions with the magnetic fields generated by the coils 106.

FIG. 1 shows two lines, each line coupled between one end of the imaging coil device 116 and the structure 102. Each line is coupled to a winch or other similar driving mechanism 128a, 128b provided to extend the mechanical line (and so the imaging coil device 116) into the bore and retract the mechanical line from the bore. In alternative embodiments, a single winch may be provided for both lines (i.e. such that the lines 120a, 120b are not separately retractable). Further, in the illustrated embodiment, force gauges 130a, 130b are provided for each line 120a, 120b, as a mechanism for determining the force or tension in the line. In the illustrated embodiment, the force gauges 130a, 130b are coupled between the respective line 120 and driving mechanism 128. In alternative embodiments, the force gauges 130 may be provided in a mount for the driving mechanism 128, to determine the force in the driving mechanism and thus the line 120.

The first and second suspension mounts 120a, 120b may be independently operable, such that the opposing ends of the imaging coil device 116 may be lowered or raised by the same or different amounts. In the latter case, the first and second suspension mounts 120a, 120b may be controlled so as to lower the imaging coil device 116 by different amounts and thus impart a tilt to the imaging coil device 116.

It will also be further noted that, although FIG. 1 shows two suspension mounts, only a single suspension mount may be provided in some embodiments. In such embodiments, the suspension mount may be coupled to the imaging coil device 116 at or towards a midpoint of the imaging coil device 116. In further alternative embodiments, more than two retractable suspension mounts 120 may be provided. In such embodiments, further controllable angular degrees of freedom (e.g., roll and pitch) are provided by providing for independent control of each mount (e.g., via separate winches for each mechanical line).

The imaging coil device 116 is further connected to the structure 102 via a constraining mechanism 118, which is operative to permit movement of the imaging coil device 116 in a restricted set of linear dimensions. In particular, in one embodiment, the constraining mechanism 118 permits movement of the imaging coil device 116 in a single linear dimension (and constrains movement of the imaging coil device 116 in other linear dimensions). In this way, the constraining mechanism 118 provides a relatively rigid connection between the imaging coil device 116 and the structure 102 as compared, for example, to the suspension mounts 120. The constraining mechanism 118 may be connected to the structure 102 by any suitable means, for example through brackets fixed to an internal surface of the structure 102, or by forming part of the structure 102 itself.

It will be noted here that the phrase "permitting movement in a single linear dimension" does not imply any limitation to movement of the imaging coil device 116 in rotational dimensions (or degrees of freedom). Rather, the constraining mechanism 118 may permit movement of the imaging coil device 116 in one or more rotational dimensions. In one embodiment, for example, the constraining mechanism 118 permits tilting of the imaging coil device 116 (e.g., such that the first end, at which the first suspension mount 120a is coupled to the imaging coil device 116, is at a different height within the bore 104 than the second end, at which the second suspension mount 120b is coupled to the imaging coil device 116).

According to embodiments of the disclosure, each of the first and second retractable suspension mounts 120a, 120b comprises a flexible mechanical line, held taut by the weight of the imaging coil device 116. Each of the first and second suspension mounts 120a, 120b, considered in isolation, therefore permits movement of the imaging coil device 116 in any dimension; however, owing to the connection to the constraining mechanism 118, movement of the imaging coil device 116 is restricted. Further, the constraining mechanism 118 may, in some embodiments, be unpowered, such that extension and/or retraction of the imaging coil device 116 is achieved through action of the one or more suspension mounts 120a, 120b.

The constraining mechanism 118 may be configured to allow movement of the imaging coil device 116 in a substantially vertical direction, i.e. lowering the imaging coil device 116 into proximity with the bed 108 (and the patient positioned on the bed), and raising the imaging coil device 116 away from the bed 108. The constraining mechanism 118 may also be configured to prevent movement of the imaging coil device in a direction along the axis of the bore, i.e. in the same longitudinal direction as movement of the bed 108. In embodiments allowing for tilting of the imaging coil device 116, the constraining mechanism 118 may be pivotally or flexibly connected to the imaging coil device 116. For example, the constraining mechanism 118 may be connected to the imaging coil device 116 by a hinge or any other suitable mechanism (e.g., a double ball joint).

The constraining mechanism 118 may comprise any mechanism which is suitable to provide such restricted movement of the imaging coil device. In one embodiment, the constraining mechanism 118 comprises a scissors mechanism, and this is shown in more detail in FIG. 2 (in cross section) and FIG. 3.

Figure 3:
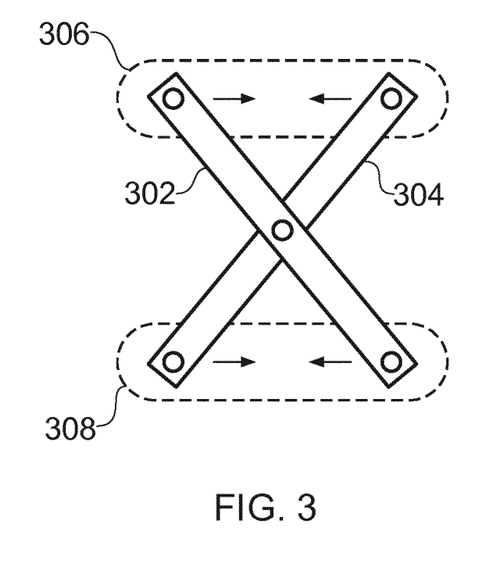
FIG. 3 shows a constraining mechanism according to embodiments of the disclosure.

FIG. 3 thus shows the scissors mechanism in more detail. First and second arms or plates 302 and 304 are rotatably coupled at a point or line of intersection with each other. For example, the point of intersection may be at or around their respective mid-points. For example, where the scissors mechanism comprises first and second plates, the line of intersection may substantially bisect each plate. The upper ends of each respective arm or plate 302, 304 may be coupled to an upper housing 306, while the lower ends of each respective arm or plate 302, 304 may be coupled to a lower housing 308. The upper housing 306 may be fixed to the structure 102 or a surface of the bore 104, and the lower housing 308 may be fixed or coupled to the imaging device coil 116.

In alternative embodiments, the constraining mechanism may comprise one or more extendible arms, arranged to extend and retract as the imaging coil device 116 is lowered or raised. For example, the arms may comprise one or more telescopic sections to allow their length to be adjusted. Those skilled in the art will appreciate that multiple different mechanisms may be used to constrain the motion of the imaging coil device to a single linear dimension.

As seen in FIG. 2, the imaging coil device 116 comprises one or more loops of wire 124 (i.e. the imaging coil itself), and associated electronic circuitry 126 coupled to the imaging coil 124 and configured to process the signals received by the loop imaging coil 124 and/or process signals for transmission by the imaging coil 124. The circuitry 126 may therefore comprise a Tx chain and/or an Rx chain comprising one or more amplifiers, and processing circuitry. The imaging coil 124 may be slightly curved (as best seen in FIG. 2), to match the contours of a patient's body.

As shown in FIG. 2, the circuitry 126 is arranged to one side of the imaging coil 124, with the majority of the footprint of the imaging coil device 16 taken up by the coil 124. According to embodiments of the disclosure, electronic circuitry is not included within the coil 124, above the coil, or below the coil. Instead, the circuitry 126 is arranged around one or more sides of the imaging coil 124.

The operation and purpose of the constraining mechanism 118 and the first and second suspension mounts 120a, 120b will now be clear. By restricting motion of the imaging coil device 116 in a direction parallel to the axis of the bore 104, the imaging coil device 116 can be positioned such that the processing circuitry 126 is never directly in line with the radiation beam 114. While the imaging coil 124 itself may lie within the path of the radiation beam (and indeed this may be desirable to achieve adequate imaging of the region undergoing therapy), the more sensitive processing circuitry does not lie within the beam's path and therefore cannot be damaged by it.

It will be appreciated by those skilled in the art that the imaging coil 124 need not be placed within the path of the radiation beam 114 in order to operate. When the gantry is rotated to certain angles, for example, the radiation beam 114 may not pass through the imaging coil 124 at all.

The system 100 further comprises a control apparatus 122, which is coupled to one or more components of the system 100 and controls their operation. The control apparatus will typically comprise a suitably programmed computing device (i.e. comprising processing circuitry configured to implement code stored in a computer-readable medium such as memory), but may also comprise dedicated electronic circuits.

The control apparatus 122 may be configured to control the operation of the radiotherapy parts of the system 100. For example, the apparatus 122 may control the source of radiation to generate a beam of therapeutic radiation having a particular energy, or comprising a particular radiation type; the apparatus 122 may control the collimator device 112 to conform the radiation beam 114 to a particular shape; the apparatus 122 may control the gantry, in order to rotate the radiation head 110 to one or more angles, such as a suitable angle for treatment; the apparatus may control movement of the bed 108 to a desired position for treatment of the patient.

The control apparatus 122 may also control the MRI parts of the system 100 so as to provide imaging information of the treatment volume of the patient. For example, the control apparatus 122 may control the magnetic coil 106 to generate a magnetic field of a certain strength, and a certain gradient; the control apparatus 122 may control the imaging coil device 116 to generate RF signals; and the control apparatus 122 may control the first and second suspension mounts 120a, 120b to control the position of the imaging coil device 116.

As discussed above, higher imaging quality is achieved when the imaging coil 124 is placed as close to the patient and the source of electromagnetic signals as possible. As the intention of the combined MRI and radiotherapy system is to provide imaging of the volume undergoing treatment, this entails placing the imaging coil 124 close to or in the path of the radiation beam 114. The interaction of the imaging coil with the radiation beam has potential problems, however. For example, secondary electrons generated by interactions between the ionizing radiation and the imaging coil may increase skin dose to the patient if the imaging coil is placed too close to or in contact with the patient.

For example, in one embodiment, the suspension mounts 120a, 120b may be controlled so as to position the imaging coil device 116 as close to the patient as possible, but without touching the patient's skin. The imaging coil device 116 may be positioned at least a predetermined minimum distance away from the patient, e.g. 5 mm, 10 mm, or 20 mm, to ensure that the patient does not come into contact with the imaging coil during therapy by making an expected movement.

In order to achieve this, each of the suspension mounts 120a, 120b may be provided with one or more force gauges which allow the force or tension in the flexible mechanical line to be determined. The output of the force [A2] gauges may be provided to the control apparatus 122. The control apparatus is operable to determine whether the imaging coil device 116 is in contact with another object (e.g. the patient) by comparing the tension in the flexible mechanical line with a predetermined threshold tension. In some embodiments the control apparatus may be operable to determine whether the imaging coil device 116 is in contact with another object by detecting a change in the tension in the flexible mechanical line. The control apparatus may be further operable to compare the tensions in the flexible mechanical lines of the first and second suspension mounts 120a, 120b to determine the position of the point of contact between the imaging coil device 122 and the object. This aspect is discussed in further detail below with respect to FIG. 4.

Figure 4:
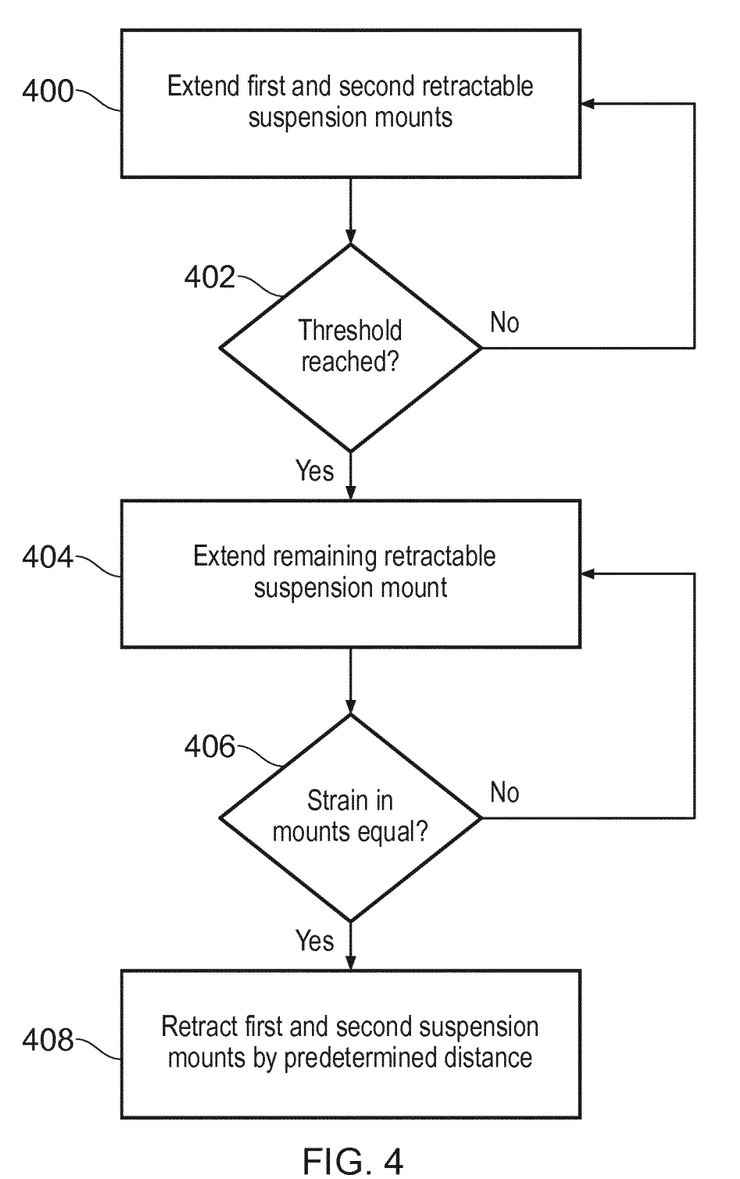
FIG. 4 is a flowchart of a method according to embodiments of the disclosure.

FIG. 4 is a flowchart of a method according to embodiments of the disclosure, of positioning the imaging coil device 116 appropriately within the bore 104 so as to image a patient undergoing therapy. The method may be performed by the control apparatus 122 described above, for example.

In a first step 400, the first and second retractable suspension mounts 120a, 120b are extended so as to lower the imaging coil device 116 into the bore 104. For example, the control apparatus may control the one or more winches 128 so as to lower the imaging coil device 116 into the bore. In a second step 402, the control apparatus 122, in communication with the one or more force gauges 130, determines whether a threshold tension has been reached in any of the flexible mechanical lines. The threshold tension may be predetermined. The threshold tension may be indicative of part of the imaging coil device 116 being in contact with or resting on another object (e.g. the patient). For example, the threshold tension may therefore be less than the tension experienced by the mechanical line under the normal load of the imaging coil device 116.

The first and second suspension mounts continue to be extended until at least one force gauge determines that the tension in at least one flexible mechanical line has reached the threshold tension. At that point, the method proceeds to step 404 [A3], where extension of the respective suspension mount is halted, and the remaining suspension mount(s), in which the threshold tension has not been reached, continue to be extended. The remaining suspension mount continues to be extended until it too reaches the threshold tension, and/or the tension in the two mechanical lines is equal (step 406). Extension of the remaining suspension mount is now halted.

As the tension in both lines is now equal, the imaging coil device 116 can be assumed to be balanced in contact with the patient. In step 408, both lines are now retracted by a predetermined amount or distance, to raise the imaging coil device 116 away from the patient. For example, the lines may be retracted by a distance sufficient to allow room for expansion and contraction of the patient's chest while breathing (e.g., 2 cm), while still keeping the imaging coil device 116 close.

It will be noted that the method of FIG. 4 may lead to the imaging coil device 116 being tilted if the suspension mounts extend by different amounts.

The present invention thus provides a combined radiotherapy and MRI system in which an imaging coil is mounted on at least one retractable suspension mount. The imaging coil is provided with a constraining mechanism. The constraining mechanism permits movement of the receiving coil device in a single linear dimension, while the at least one retractable suspension mount comprises a flexible mechanical line held under tension by the weight of the imaging coil device. The imaging coil device is thus robustly held in place without significantly complex mechanisms. Further, any electrical control components for the flexible mechanical lines (e.g., motors, winches, force gauges, etc) can be located sufficiently far from the apparatus so as not to interfere with the magnetic field of the MRI system.

Those skilled in the art will appreciate that various amendments and alterations can be made to the embodiments described above without departing from the scope of the invention as defined in the claims appended hereto.

The invention claimed is:

1. A medical apparatus, comprising:
a structure defining a bore in which a patient or part of a patient can be positioned during use;
an MRI system comprising:
a receiving coil device positioned within the bore, the receiving coil device comprising a receiving coil for detecting radio signals emitted by relaxing nuclei within the patient;
a constraining mechanism coupled between the structure and the receiving coil device, the constraining mechanism permitting movement of the receiving coil device in a single linear dimension;
one or more retractable suspension mounts, each of the one or more retractable suspension mounts comprising a flexible line arranged to suspend at least part of the receiving coil device within the bore; and
control circuitry operable to control each of the one or more retractable suspension mounts, wherein the control circuitry is operable to:
extend the flexible line of each of the one or more retractable suspension mounts until a tension in the respective flexible line reaches a predetermined threshold; and
responsive to a determination that the tension in the respective flexible line has reached the predetermined threshold, retract one or more of the one or more retractable suspension mounts a predefined distance.

2. The medical apparatus according to claim 1, wherein the constraining mechanism is retractable.

3. The medical apparatus according to claim 2, wherein the constraining mechanism comprises a scissors mechanism.

4. The medical apparatus according to claim 3, wherein the scissors mechanism comprises first and second intersecting arms, rotatably coupled to each other at a point of intersection.

5. The medical apparatus according to claim 1, wherein the constraining mechanism permits tilting of the receiving coil device.

6. The medical apparatus according to claim 1, wherein the constraining mechanism is unpowered.

7. The medical apparatus according to claim 1, wherein at least one retractable suspension mount comprises a first retractable suspension mount and a second retractable suspension mount, the first retractable suspension mount coupled to the receiving coil device at or towards a first end of the receiving coil device, and the second retractable suspension mount coupled to the receiving coil device at or towards a second, opposing end of the receiving coil device.

8. The medical apparatus according to claim 1, wherein the one or more flexible lines are coupled to one or more winches for extension or retraction of the one or more flexible lines.

9. The medical apparatus of claim 8, wherein the one or more winches are operable to raise or lower the receiving coil device by extending or retracting the one or more flexible lines.

10. The medical apparatus according to claim 8, wherein the one or more winches are located outside the bore.

11. The medical apparatus according to claim 1, wherein each of the one or more suspension mounts is operable independently of each other.

12. The medical apparatus according to claim 1, further comprising:
a source of radiation, for generating a beam of therapeutic radiation that passes through a radiation volume.

13. The medical apparatus according to claim 12, wherein the receiving coil device further comprises processing circuitry located at one or more of first and second ends of the receiving coil device.

14. The medical apparatus according to claim 13, wherein the receiving coil device is positioned in the bore such that the receiving coil lies within the radiation volume, while the processing circuitry lies outside the radiation volume.

15. A method comprising:
providing a structure defining a bore in which a patient or part of a patient can be positioned during use;
providing an MRI system comprising:
a receiving coil device positioned within the bore, the receiving coil device comprising a receiving coil for detecting radio signals emitted by relaxing nuclei within the patient;
a constraining mechanism coupled between the structure and the receiving coil device, the constraining mechanism permitting movement of the receiving coil device in a single linear dimension; and
one or more retractable suspension mounts, each of the one or more retractable suspension mounts comprising a flexible line arranged to suspend at least part of the receiving coil device within the bore;
extending the flexible line of each of the one or more retractable suspension mounts until a tension in the respective flexible line reaches a predetermined threshold; and
responsive to a determination that the tension in the respective flexible line has reached the predetermined threshold, retract one or more of the one or more retractable suspension mounts a predefined distance.

16. The method of claim 15, wherein the constraining mechanism is retractable.

17. The method of claim 16, wherein the constraining mechanism comprises a scissors mechanism.

18. The method of claim 15, wherein the constraining mechanism permits tilting of the receiving coil device.

19. An apparatus comprising:
means for providing a structure means defining a bore in which a patient or part of a patient can be positioned during use;
means for providing an MRI system means comprising:
a receiving coil device means positioned within the bore, the receiving coil device comprising a receiving coil for detecting radio signals emitted by relaxing nuclei within the patient;
a constraining mechanism means coupled between the structure and the receiving coil device, the constraining mechanism permitting movement of the receiving coil device in a single linear dimension; and
one or more retractable suspension mounts means, each of the one or more retractable suspension mounts comprising a flexible line arranged to suspend at least part of the receiving coil device within the bore;
means for extending the flexible line of each of the one or more retractable suspension mounts until a tension in the respective flexible line reaches a predetermined threshold; and
means for responsive to a determination that the tension in the respective flexible line has reached the predetermined threshold, retract one or more of the one or more retractable suspension mounts a predefined distance.

20. The apparatus of claim 19, wherein the constraining mechanism means is retractable.

\* \* \* \* \*